United States Patent [19]

Boschetti

[11] Patent Number: 5,342,308
[45] Date of Patent: Aug. 30, 1994

[54] SINGLE-USE SYRINGE WITH RETRACTABLE NEEDLE

[75] Inventor: Vittorio Boschetti, Brebbia, Italy

[73] Assignee: BRIEF S.r.l., Milan, Italy

[21] Appl. No.: 721,487

[22] PCT Filed: Nov. 20, 1989

[86] PCT No.: PCT/EP89/01408
§ 371 Date: Jul. 10, 1991
§ 102(e) Date: Jul. 10, 1991

[87] PCT Pub. No.: WO90/00614
PCT Pub. Date: Jun. 14, 1990

[30] Foreign Application Priority Data

Dec. 1, 1988 [IT] Italy .................. 22810 A/88

[51] Int. Cl.⁵ .................................. A61M 5/00
[52] U.S. Cl. .......................... 604/110; 604/198; 604/263
[58] Field of Search ............ 604/110, 187, 192, 195, 604/196, 198, 218, 220-222; 128/917

[56] References Cited

U.S. PATENT DOCUMENTS

| | | | |
|---|---|---|---|
| 4,747,829 | 5/1988 | Jacob | 604/110 |
| 4,767,413 | 8/1988 | Haber et al. | 604/198 |
| 4,775,369 | 10/1988 | Schwartz | 604/263 |
| 4,921,486 | 5/1990 | DeChellis et al. | 604/110 |
| 4,955,869 | 9/1990 | Bin | 604/195 |
| 5,026,353 | 6/1991 | Bartman | 604/192 |
| 5,114,404 | 5/1992 | Payton | 604/110 |

FOREIGN PATENT DOCUMENTS

| | | | |
|---|---|---|---|
| 0364387 | 4/1990 | European Pat. Off. | 604/110 |
| 3808688 | 1/1989 | Fed. Rep. of Germany | 604/198 |
| 2243552 | 11/1991 | United Kingdom | 604/110 |

Primary Examiner—John D. Yasko
Assistant Examiner—V. Alexander
Attorney, Agent, or Firm—Sughrue, Mion, Zinn, Macpeak & Seas

[57] ABSTRACT

The syringe has a tubular body slidably housing a plunger connected to a needle, movable between a first, safe position and a second, working position, respectively retracted into and extended from the body, and a spring biasing the needle toward its retracted position. An expansible retaining member is attached to one end of the needle and overrides a step, defined on the tubular body, as the needle is moved from the first to the second position. An expander device is carried movably on the plunger and adapted to be received and held in a socket formed in the retaining member to expand it and hold the needle in the working position. An annular rib is provided on a lug connected to the plunger for dislodging the retaining member from the step and release the needle, which is returned by the spring to its first position, out of sight inside the tubular body.

14 Claims, 3 Drawing Sheets

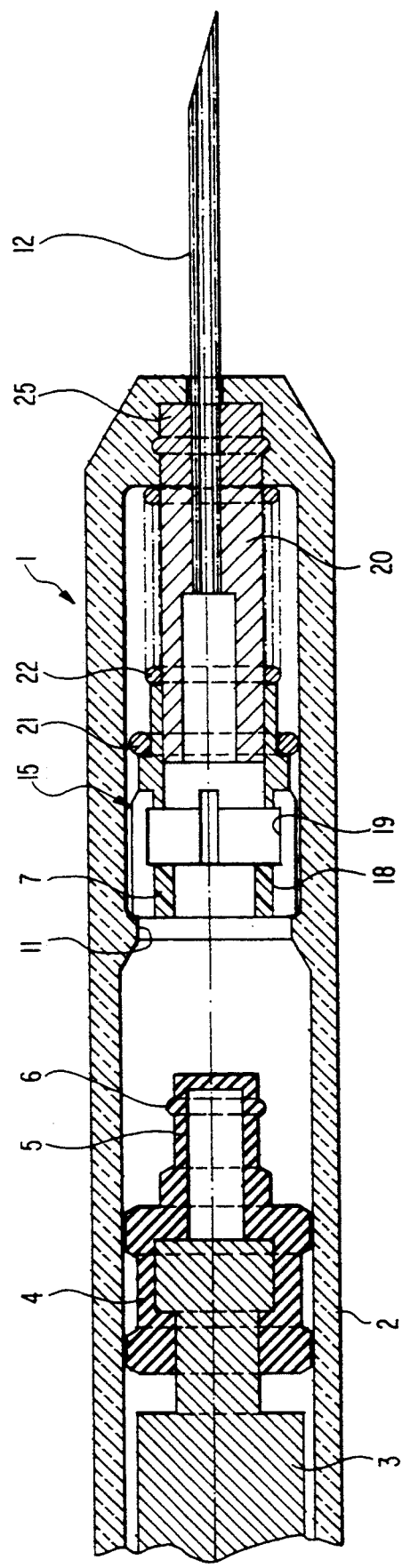
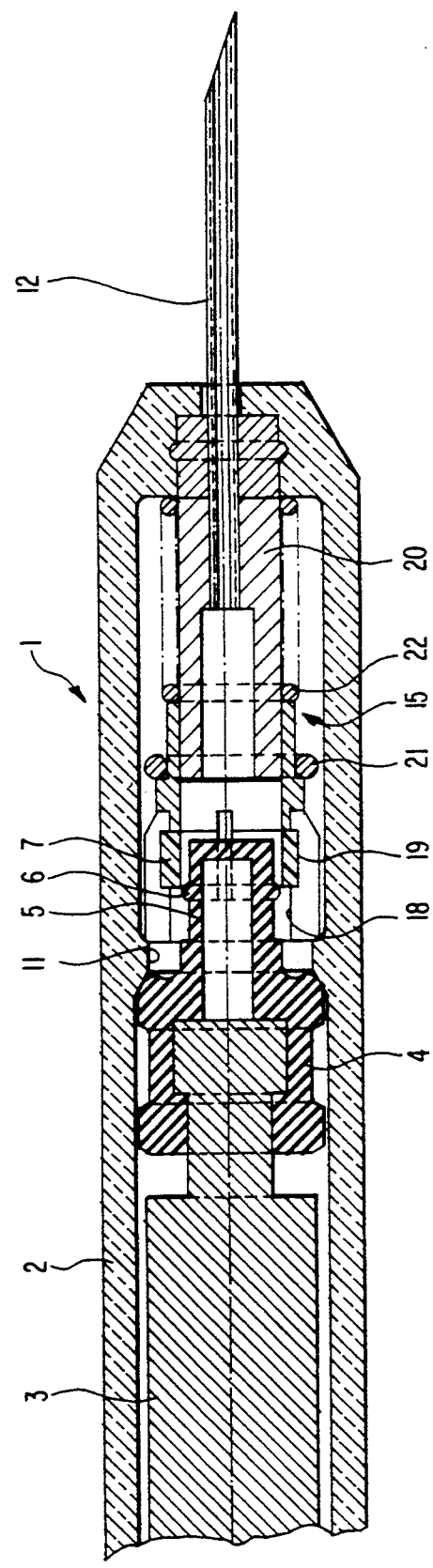

SINGLE-USE SYRINGE WITH RETRACTABLE NEEDLE

BACKGROUND OF THE INVENTION

This invention relates to a single-use syringe of a type which comprises a tubular body wherein a plunger is slidable in sealed relationship, a needle mounted in said tubular body at a first axial end thereof and being movable between a first, safe position and a second, working position whereat said needle is retracted into and extended from said body, respectively, through an opening in the latter, a spring biasing said needle toward its retracted position, said needle being temporarily lockable in its working position.

Re-use of a syringe by many is one of the factors that promotes the spreading of diseases whose infection is passed on by contact with infected blood.

Typical is the spreading of AIDS among people addicted to injectable drugs, where there is a habit of sharing one syringe with several persons.

The most popular of know syringes, while explicitly intended for single use, may nevertheless be used more than once without impairing their mechanical efficiency.

Further, and besides the risk represented by possible re-use thereof, such syringes involve a serious risk of incidental pricking because the needle is left exposed on the tubular body after use of the syringe with no safeguard of sort.

In an effort to obviate such drawbacks, syringes have been developed which incorporate provisions to prevent their re-use and/or a retractable needle, to thereby eliminate the risks connected with the handling of a used syringe.

Typical examples of such improved syringes are described in U.S. Pat. Nos. 4,675,005; 4,747,829; 4,692,156; PCT Application No. W088/06461; European Patent Application No. 282097; and U.S. Pat. No. 4,747,830.

However, it has been found that the engineering of these prior types of syringes has resulted in relatively elaborate constructions, quite unsuited to syringes which may be small in size as are use, in particular, by drug addicts. In addition, some of these syringes can be returned to a working condition after use by relatively simple operations to permit their re-use.

The problem underlying this invention is to provide a single-use syringe which is structured and operated in such a manner as to first eliminate any problems in handling a used syringe, and secondly, make re-use of the syringe practically impossible.

SUMMARY OF THE INVENTION

This problem is solved according to the invention by a syringe which comprises an expansible retaining member attached to one end of the needle extending inside said tubular body, at least one step defined in said tubular body at a set distance from said first end, wherefore said step is overridden by said retaining member as said needle is moved from said first to the second position, an expander device for the retaining member carried removably on said plunger and adapted to be received and held in a first socket of the retaining member so as to expand it upon the step being overridden and hold the needle in the working position with said retaining member abutted against the step, and a means of dislodging the expander device from the first socket on completion of a working stroke of the plunger so as to disengage the retaining member from the step and release the needle for return to the first position.

BRIEF DESCRIPTION OF THE DRAWINGS

The features and advantages of this invention will be more clearly apparent fromt he following detailed description of a preferred, but not exclusive, embodiment thereof, shown by way of non-limitative example in the accompanying drawings, where:

FIGS. 1 to 5 are fragmentary sectional views of a syringe embodying this invention, shown at various stages of its operation.

DESCRIPTION OF THE PREFERRED EMBODIMENTS

Figure 1:
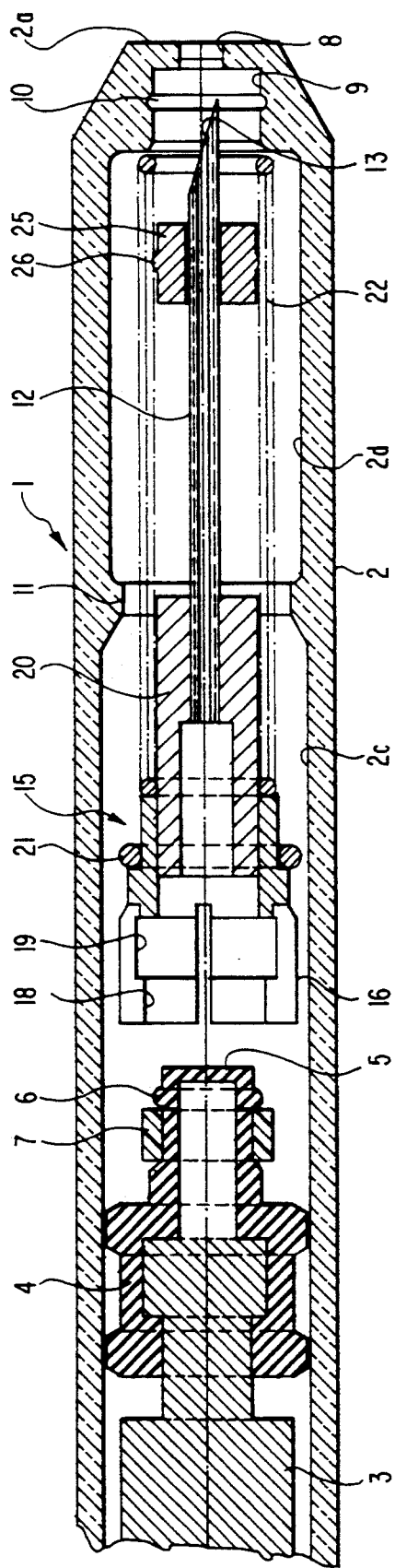

Generally indicated at 1, in FIGS. 1 to 5, is a syringe according to this invention. The syringe 1 comprises a tubular body 2 wherein a plunger 3 is slidable in sealed relationship and is provided, at an axial end thereof, with a piston 4 made of a soft elastomeric material.

A lug 5 extends in axial continuation of the piston 4 and is a unitary construction therewith.

The lug 5 is substantially cylindrical in shape, hollow inside, and carries an annular ridge 6 on its free end which defines a groove which removably accommodates a ring 7 made of a rigid plastic material.

An opening 8 is formed at an axial end 2a of the tubular body 2 which widens out, on the side facing inwards of the tubular body, into a first socket 9 whose function will be explained hereinafter.

A narrow circumferential groove 10 is formed in the wall of the first socket 9.

An annular step 11 is formed on the interior of the tubular body 2 at a set axial distance fromt he end 2a.

The step 11 bounds two contiguous cylindrical sections inside the tubular body, which have different inside diameters 2c and 2d, respectively.

A hollow needle 12 is supported slidably within the tubular body 2. A tip 13 is defined at one end thereof, and a retaining member, generally indicated at 15, is attached to the other end of the needle.

The retaining member 15 comprises a needle-holding head 20 substantially cylindrical in shape, and a bell 16 formed with longitudinal cuts 17 effective to confer elasticity on the bell, in the radial direction thereof.

Inside the bell 16, there are defined second and third sockets, respectively indicated at 18 and 19, which have different inside diameters.

The second and third sockets 18, 19 are adapted to accommodate the ring 7, respectively in interference fit and limited radial clearance relationship. The ring 7, when received in the socket 18, behaves as an expander device for the bell 16.

A ring seal 21 is fitted over the bell 16 outside, at a recessed region on the latter. The seal 21 is adapted to make a seal with the inner wall of the tubular body 2 at the section 2d thereof.

A coil spring 22 is interposed to the end 2a of the tubular body 2 and the member 15 to bias the needle 12 toward a first or safe position of retraction inside the tubular body.

Supported in between the turns of the spring 22 is a needle-guiding member 245 which fits slidably over the needle 12 and is adapted to snap into the socket 9 with an annular ridge 26 inserted into the circumferential groove 10.

The thrust force from the spring 22 biases the needle 12 toward a position offset from the axis of the opening 8; however, this bias is resisted before use of the syringe 1 by the needle-guiding member 25.

Figure 2:
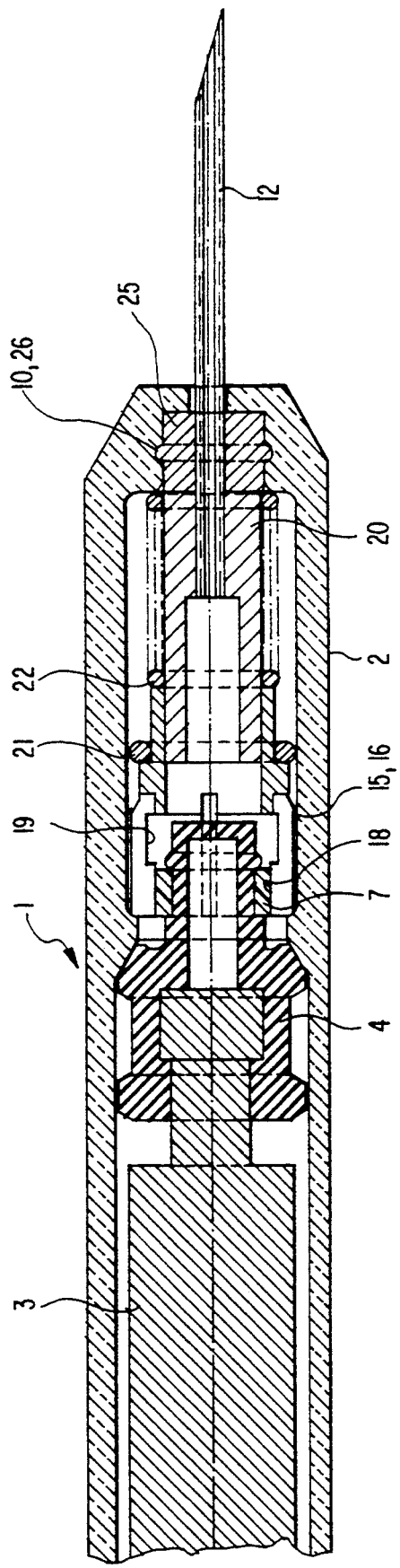
Figure 5:
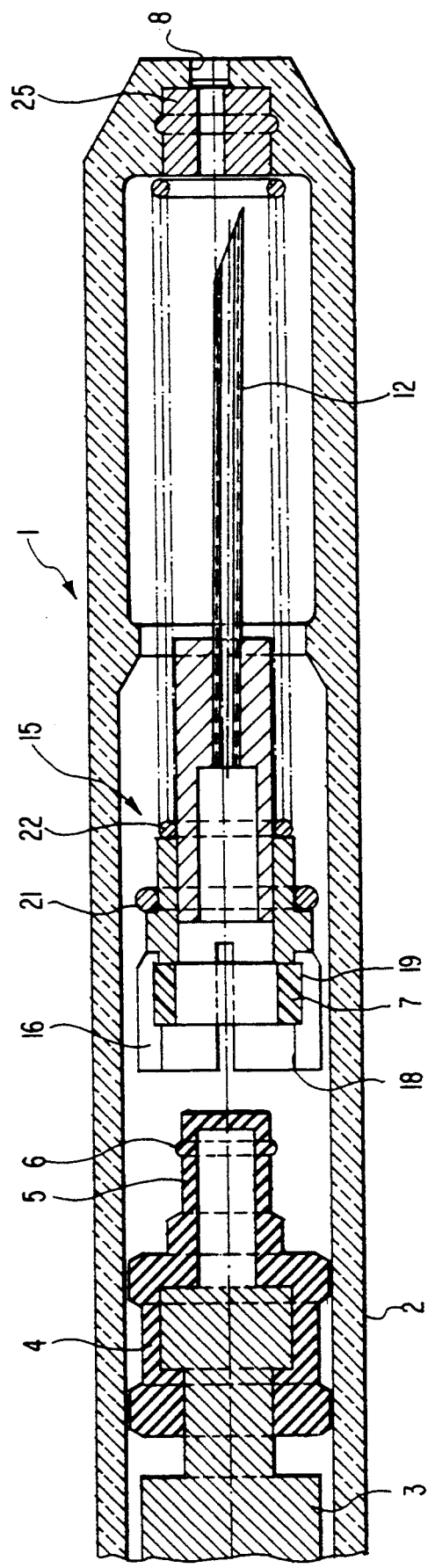

In its for-sale condition, the syringe would have the configuration shown in FIG. 1. To use the syringe, one should move the needle 12 from its safe retracted position inside the tubular body 2 to a second or working position, as shown in FIG. 2.

On pushing the plunger 3 toward the end 2a of the tubular body, the retainer 15 will be urged by the piston 4, and specifically by the ring 7 carried on the lug 5, in a direction toward the step 11 against the bias of the spring 22. At the same time, the needle 12 will move outwardly through the opening 8.

Because of the interference between the second socket 18 of the bell 16 and the ring 7, the latter will remain, at this stage of preparation of the syringe 1 for use, in its abutted condition against the corresponding end of the bell 16 unit the needle-guiding member 25 is pushed into the first socket 9 of the body 2 and, simultaneously therewith, the bell 16 contracts radially and moves past the step 11.

By a further push on the plunger 3, the ring 7 is then forced to engage the second socket 18 formed in the retainer 15, and to be held therein to hold the bell 16 expanded radially.

The syringe 1 is now ready for use (position shown in FIG. 2).

By drawing the plunger 3 away fromt he end 2a, the ring 7 is cased to stay engaged in the second socket 18, thereby the needle 12 cannot be retracted by the bias applied by the spring 22.

At this stage, a liquid may be drawn into the tubular body, through the needle 12, into the chamber defined between the piston 4 and the seal 21. The syringe 1 will behave like an ordinary fixed needle disposable syringe (FIG. 3).

To inject the drawn liquid by a subsequent working stroke of the plunger 3 (FIG. 4), the plunger is again pushed in toward the end 2a of the tubular body until the annular ridge 6 of the lug 5 contacts the ring 7 held in the first socket 18 of the retainer.

A further push on the plunger 3 will cause the ring 7 to become dislodged from the second socket 18 and move into the third socket 19. In view of the fact that the ring 7 is received with some radial clearance in the third socket 19, the bell 16, which is still held abutted on the step 11 by the spring 22, is now free to contract.

Thus, on releasing the pressure exerted on the plunger 3, the needle 12 and the retainer 15 associated therewith will be retracted into the first, safe position, out of sight inside the tubular body 2.

Since the needle-guiding member 25 is held back in the first socket 9, the needle 12 will be drawn out of it, and being no longer guided, diverted by the thrust component from the spring 22 to an offset position fromt he axis of the opening 8.

Thus, any further attempts at extending the needle 12 by a push exerted on the plunger 3 would be ineffective.

Figure 6:
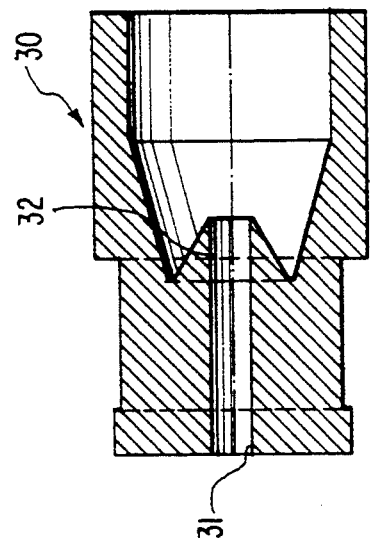
FIG. 6 is a longitudinal section view of a modified embodiment of a detail of the syringe shown in the previous Figures.

FIG. 6 shows a modified embodiment of the needle-guiding member. In this modified embodiment, which is provided to further enhance the ability to prevent a second extension of the needle 12 out of the tubular body 2, the needle-guiding member is generally denoted by the numeral 30.

The outward configuration of the member 30 requires that the first socket 9 be shaped differently, as may be appreciated by one skilled in the art, to enable said member 30 to be received therein in matching shape relationship.

The member 30 is through-penetrated by an axial bore 31 and has, on the side facing toward the interior of the tubular body 2, a conical projection 32 extending around the opening of the bore 31.

Defined around the projection 32 is a recess having flared walls 33 effective to catch and hold the tip 13 of the needle 12 after use of the syringe and with the needle fully retracted into the tubular body 2, in the event of any attempt to re-use the syringe 1.

The major advantage of the syringe according to the invention is that it is highly reliable in operation and quite safe for the user. Almost all of its components can be readily manufactured by a molding process form suitable plastics materials, as conventionally used in the manufacture of disposable syringes.

The simple construction also permits syringes to be manufactured in any size at relatively low production costs.

Furthermore, it should be noted that the further push on the plunger required to move the ring 7 into the socket 19, so that the needle can be allowed to move back into its retraced position, is advantageous because of the fact that a significant amount of the liquid drawn up into the tubular body would not be injected otherwise. With drugs, the worth of the residual liquid would exceed the cost of the syringe by an appreciable amount.

What is claimed is:

1. A single-use syringe comprising a tubular body, a plunger slidable in sealed relationship within said tubular body, a needle mounted in said tubular body at a first axial end thereof and being movable between a first, safe position and a second, working position whereat said needle is retracted into and extended from said body, respectively, through an opening of the body, a first socket formed in said tubular body, needle guide means carried by said needle and received in said first socket for guiding said needle through said opening, an expansible and contractible retaining member attached to one end of the needle extending inside said tubular body, spring biasing said retaining member and said needle toward said retracted safe position, at least one step defined in said tubular body at a set distance from said first end, said step being overridden by said retaining member as said needle is moved from the first to the second position, an expander device for expanding the retaining member carried removably on said plunger and received and held in a second socket formed in said retaining member so as to expand said retaining member upon overriding the step to hold the needle in the working position with said retaining member abutted against the step, means on said plunger for dislodging the expander device from said socket means on completion of a working stroke of the plunger so as to disengage the retaining member from the step and allow said spring to return the needle to the first retracted position, and means for misaligning said needle, upon return to said first retracted position, with respect to said opening wherein reuse of said syringe is prevented.

2. A syringe according to claim 1, wherein said means for misaligning said needle with respect to said opening are constituted by means in said first socket which engages and retains said needle guide means in said first socket upon returning said needle to said first position, and wherein said retaining member comprises a bell open to said plunger, said bell comprising said second socket and a third socket, said third socket being configured to accommodate said expander device when dislodged from said second socket to permit said retaining member to contract.

3. A syringe according to claim 2, wherein said bell is formed with longitudinal cuts.

4. A syringe according to claim 1, wherein said expander device for the retaining member comprises a ring held removably on a plunger lug.

5. A syringe according to claim 4, wherein said means for dislodging the expander device from said second socket comprises said plunger lug.

6. A syringe according to claim 5, wherein said plunger lug has a substantially cylindrical shape and is provided with an annular ridge which holds said ring on said lug until said ring is received in said second socket.

7. A syringe according to claim 4, wherein said lug is of unitary construction with a piston of the plunger.

8. A syringe according to claim 7, wherein the retaining member comprises a head which pushed the needle-guiding member into said first socket with the needle in its second position.

9. A syringe according to claim 1, wherein said needle guide means comprises a needle-guiding member detachably mounted on said needle and is to be pushed into engagement with and held in said first socket formed at the first end of the tubular body.

10. A syringe according to claim 9, wherein said spring is a coil spring, and said needle-guiding member is held in said coil spring prior to being received in said first socket, thereby aligning said needle to the opening in said first end of the tubular body.

11. A syringe according to claim 10, wherein the needle-guiding member has, on its side facing the retaining member, a conical profile shape.

12. A syringe according to claim 11, wherein said needle, in its retracted position inside the tubular body following a working stroke of the plunger, is disengaged from the needle-guiding member and offset from the opening of the tubular body.

13. A syringe according to claim 1, wherein said needle, in its retracted position inside the tubular body following a working stroke of the plunger, is offset from the opening of the tubular body.

14. A syringe according to claim 1, wherein the retaining member is engaged in said tubular body between said step and said first axial end in sealed relationship therewith.

* * * * *